(12) United States Patent
Yamada et al.

(10) Patent No.: US 9,183,757 B2
(45) Date of Patent: Nov. 10, 2015

(54) DIETING SUPPORT SYSTEM AND DIETING SUPPORT METHOD

(75) Inventors: Yuuki Yamada, Chiyoda-ku (JP); Satoshi Hiyama, Chiyoda-ku (JP)

(73) Assignee: NTT DOCOMO, INC., Tokyo (JP)

( * ) Notice: Subject to any disclaimer, the term of this patent is extended or adjusted under 35 U.S.C. 154(b) by 195 days.

(21) Appl. No.: 13/979,458

(22) PCT Filed: Sep. 4, 2012

(86) PCT No.: PCT/JP2012/072502
§ 371 (c)(1),
(2), (4) Date: Jul. 12, 2013

(87) PCT Pub. No.: WO2013/038959
PCT Pub. Date: Mar. 21, 2013

(65) Prior Publication Data
US 2013/0288208 A1    Oct. 31, 2013

(30) Foreign Application Priority Data
Sep. 14, 2011  (JP) .................................. 2011-201180

(51) Int. Cl.
*G09B 19/00* (2006.01)
*G06F 19/00* (2011.01)
*G06Q 50/22* (2012.01)

(52) U.S. Cl.
CPC ........ *G09B 19/0092* (2013.01); *G06F 19/3475* (2013.01); *G06Q 50/22* (2013.01); *G06F 19/3481* (2013.01)

(58) Field of Classification Search
CPC ............... G06F 19/3481; G06Q 50/22; G09B 19/0092; G09B 19/00

USPC ......................................................... 434/127
See application file for complete search history.

(56) References Cited

U.S. PATENT DOCUMENTS

2004/0186390 A1*  9/2004  Ross et al. ..................... 600/532

FOREIGN PATENT DOCUMENTS

| JP | 11 328122 | 11/1999 |
|----|-----------|---------|
| JP | 2001 349888 | 12/2001 |
| JP | 2003 79601 | 3/2003 |
| JP | 2008 295921 | 12/2008 |
| JP | 2010 268864 | 12/2010 |
| JP | 2012 11133 | 1/2012 |

OTHER PUBLICATIONS

"Exercise and Physical Activity Guide for Health Promotion 2006", Exercise Guide 2006, Total 9 Pages, (2006) (with English translation).
Kundu, S., et al., "Breath Acetone Analyzer: Diagnostic Tool to Monitor Dietary Fat Loss", Clin. Chem., vol. 39, No. 1, pp. 87-92, (1993).
International Search Report Issued Nov. 27, 2012 in PCT/JP12/072502 Filed Sep. 4, 2012.
Office Action issued Jul. 1, 2014 in Japanese Patent Application No. 2013-533624 (with English language translation).

* cited by examiner

*Primary Examiner* — Peter Egloff
*Assistant Examiner* — Robert P Bullington
(74) *Attorney, Agent, or Firm* — Oblon, McClelland, Maier & Neustadt, L.L.P.

(57) ABSTRACT

A dieting support system includes a function that detects a component of biogas and that measures concentration of the biogas, a function that accumulates and analyzes the measured result, and a function that determines suitable timing for taking a meal or suitable timing for doing exercise, depending on the analyzed result.

12 Claims, 12 Drawing Sheets

FIG.4

| TIME OF MEASUREMENT | ACETONE CONCENTRATION [ppb] | ETHANOL CONCENTRATION [ppb] |
|---|---|---|
| 8/17/2011 7:00:01 | 900 | 0 |
| 8/17/2011 8:01:11 | 842 | 235 |
| 8/17/2011 9:05:11 | 675 | 111 |
| 8/17/2011 10:21:32 | 743 | 0 |
| 8/17/2011 11:04:53 | 900 | 0 |
| 8/17/2011 12:01:11 | 910 | 0 |
| 8/17/2011 13:32:14 | 675 | 450 |
| 8/17/2011 14:42:37 | 565 | 230 |
| 8/17/2011 15:25:52 | 434 | 0 |
| 8/17/2011 16:35:17 | 333 | 0 |
| 8/17/2011 17:32:51 | 403 | 0 |
| 8/17/2011 18:41:34 | 689 | 0 |
| 8/17/2011 19:47:41 | 988 | 0 |
| 8/17/2011 20:38:51 | 530 | 531 |
| 8/17/2011 21:47:11 | 323 | 270 |
| 8/17/2011 22:17:25 | 333 | 0 |
| 8/17/2011 23:58:53 | 454 | 0 |
| 8/18/2011 00:38:43 | 484 | 0 |
| 8/18/2011 7:28:43 | 888 | 0 |
| 8/18/2011 8:36:23 | 674 | 232 |
| 8/18/2011 9:34:51 | 545 | 50 |

FIG.5

| USER NAME | GENDER | BODY FAT PERCENTAGE [%] | BMI |
|---|---|---|---|
| AAA | MALE | 21.5 | 23.2 |
| BBB | FEMALE | 25.4 | 23.4 |
| CCC | FEMALE | 24.3 | 20.5 |
| DDD | MALE | 14.2 | 19.3 |
| EEE | MALE | 30.1 | 29.3 |
| FFF | MALE | 5.6 | 17.3 |
| GGG | FEMALE | 38.7 | 32.3 |
| HHH | MALE | 19.3 | 22.0 |
| III | FEMALE | 18.2 | 21.8 |

DIETING SUPPORT SYSTEM AND DIETING SUPPORT METHOD

TECHNICAL FIELD

The present invention relates to a dieting support system and a dieting support method which are based on measurements and analyses of components of biogas. Further, the present invention relates to a terminal device and a server that can be used for the dieting support system and the dieting support method.

BACKGROUND ART

Due to a recent health boom, various dieting methods for an obesity resolution appear and go off, and topics are not exhausted. It implies that there are no universal dieting methods which are effective for everybody, and that there is a need for providing custom-made dieting methods that are suitable for individuals. A principle of the dieting is simple. Namely, when burned calories are greater than consumed calories, body weight is reduced. In other words, what is important for dieting is a proper meal which is suitable for an individual, and further a combination of the proper meal which is suitable for the individual and exercise (cf. "Exercise and Physical Activity Guide for Health Promotion 2006—To Prevent Lifestyle-related Diseases—<Exercise Guide 2006>," prepared by the Ministry of Health, Labour and Welfare of Japan, for example).

Regarding the meal, it has been known that not only reducing the consumed calories, but also taking the meal at proper timing, not in accordance with a clock, are effective for the dieting. Namely, it has been known that taking the meal during fasting is effective for the dieting. Although a brain can detect whether it is fasting, feelings of hunger/fullness are subjective, and it has been known that the feelings of hunger/fullness do not always accurately reflect a state in a body such as an amount of glycogen stored in a body and a level of glucose in blood at that time. In fact, the feeling of fullness tends to be easily obtained by increasing a number of times of chewing, and the feeling of hunger is not sensed during concentrating on a task. These show that the brain tends to be easily confused. Whereas, by measuring the level of glucose in the blood, it is possible to objectively understand the feeling of hunger. However, since this method involves collection of the blood, it is not easily performed by a typical individual. Thus, there is a need for a measure to objectively and easily understand the feeling of hunger and to find suitable timing for taking the meal.

Meanwhile, regarding exercise, doing exercise during fasting is more effective for the dieting. That is because the amount of glycogen stored in the body is small, and fat (e.g., visceral fat) tends to be easily burned. Further, regarding the exercise, quality and quantity of the exercise to be done is important. It is effective for the dieting to do exercise at proper exercise intensity that matches with an individual for a proper time period. There is an individual difference in endurance to the exercise. The fat does not burn when an exercise load is too large, or when the exercise load is too small.

Conventionally, it has been known that a fat-burning condition can be confirmed by measuring and analyzing components of biogas discharged from a living body. For example, Patent Document 1 discloses a method of confirming a burning condition of body fat by measuring an acetone level included in breathing gas. Further, Patent Document 2 discloses a method of calculating exercise intensity for efficiently burning the body fat by measuring an acetone level included in the breathing gas. Acetone is one of metabolic products associated with decomposition of the body fat. Though it is an infinitesimal quantity, acetone is included in the breathing gas and a gas component discharged from skin and a mucous membrane. Accordingly, acetone has a potential to be a marker for fat burning, which can be easily measured by an individual.

However, both Patent Document 1 and Patent Document 2 disclose nothing regarding a measure and a method for reporting suitable timing for taking the meal and suitable timing for doing exercise to an individual. Besides, these documents do not mention anything regarding a measure and a method for estimating a quantity of exercise in a predetermined time period and for advising an individual to improve lifestyle, so that a usual acetone concentration level is increased.

RELATED ART DOCUMENT

Patent Document

Patent Document 1: Japanese Unexamined Patent Publication No. 2001-349888
Patent Document 2: Japanese Unexamined Patent Publication No. 2010-268864

Non-Patent Document

"Exercise and Physical Activity Guide for Health Promotion 2006—To Prevent Lifestyle-related Diseases—<Exercise Guide 2006>," prepared by the Ministry of Health, Labour and Welfare of Japan

SUMMARY OF THE INVENTION

Problem to be Solved by the Invention

An object of the present invention is to provide a dieting support system and a dieting support method that easily and objectively measure a degree of hunger of an individual and that report information regarding suitable timing for taking a meal and a recommended meal. Further, another object of the present invention is to provide the dieting support system and the dieting support method that report suitable timing for doing exercise, exercise intensity, and an exercise time period, where a dieting effect (a fat burning effect) is expected to be high, to the individual. Furthermore, another object of the present invention is to provide the dieting support system and the dieting support method that estimate a fat-burning condition and a quantity of the exercise of the individual during a predetermined time period, and that advises, as a so-called "guideline for daily activity" of the individual, an improvement of lifestyle, so that a usual acetone concentration level becomes high.

Means for Solving the Problem

As a result of making extensive studies, the inventors found that, by detecting various components of biogas discharged from a living body of the individual, by measuring the concentration of the biogas, and by analyzing the measurement result, a degree of hunger of the individual can be easily and objectively understood. Information regarding suitable timing for taking a meal and a recommended meal can be reported to the individual. Timing, exercise intensity, and a time period for doing the exercise, with which a dieting effect (a fat burning effect) is high, can be reported to the individual. Furthermore the inventors found that a fat-burning condition and a quantity of the exercise of the individual during a predetermined time period can be estimated, and thereby the inventors accomplished the present invention.

Namely, a dieting system according to the present invention is characterized in that it includes a function of detecting components of biogas and measuring concentration of the biogas; a function of accumulating and analyzing the measurement result; and a function of determining timing which is suitable for taking a meal or timing which is suitable for doing exercise, depending on the result of the analysis.

Further, a terminal device according to the present invention is characterized in that it includes a function of detecting biogas discharged from a living body, measuring concentration of the biogas, and transmitting a measurement result to outside; and a function of receiving a message regarding timing which is suitable for taking a meal or suitable for doing exercise, a recommended meal, recommended exercise, a recommended lifestyle, or a fat-burning condition.

Further, a server according to the present invention is characterized in that it includes a function of receiving a result of measured biogas which is discharged from a living body; a function of accumulating and analyzing the received measurement result of the biogas; a function of determining timing which is suitable for taking a meal or timing which is suitable for doing exercise, a recommended meal, a recommended exercise, a recommended lifestyle, or a fat-burning condition; and a function of transmitting a message regarding the timing which is suitable for taking the meal or the timing which is suitable for doing exercise, the recommended meal, the recommended exercise, the recommended lifestyle, or the fat-burning condition.

Further, a dieting support method according to the present invention is characterized in that a computer executes a step of detecting components of biogas which is discharged from a living body and measuring concentration of the components of the biogas, a step of accumulating and analyzing the measurement result; and a step of reporting timing which is suitable for taking a meal or doing exercise, a recommended meal, a recommended exercise, a recommended lifestyle, or a fat-burning condition.

Effect of the Present Invention

According to the present invention, a degree of hunger of a user can be objectively and easily understood, and a user can become aware of the information regarding the timing which is suitable for taking the meal and the recommended meal. Further, the user can become aware of the timing suitable for doing the exercise, the exercise intensity, and the time period for doing the exercise, where the fat-burning effect is expected to be high. Namely, there can be provided the custom-made dieting support program which reflects a metabolic condition of an individual.

BRIEF DESCRIPTION OF THE DRAWINGS

FIG. 4 is an example of a user AAA's biogas concentration database according to the embodiment of the present invention;

FIG. 5 is an example of a personal information database according to the embodiment of the present invention;

EMBODIMENTS FOR CARRYING OUT THE INVENTION

Hereinafter, an embodiment of the present invention is explained in detail.

In the explanation of the present specification, a user and a target person of a dieting support system or a dieting support method in the embodiment of the present invention are sometimes exemplarily denoted as an "individual" or the "user." However, the dieting support system or the dieting support method is not limited by these.

(Dieting Support System)

Figure 10:
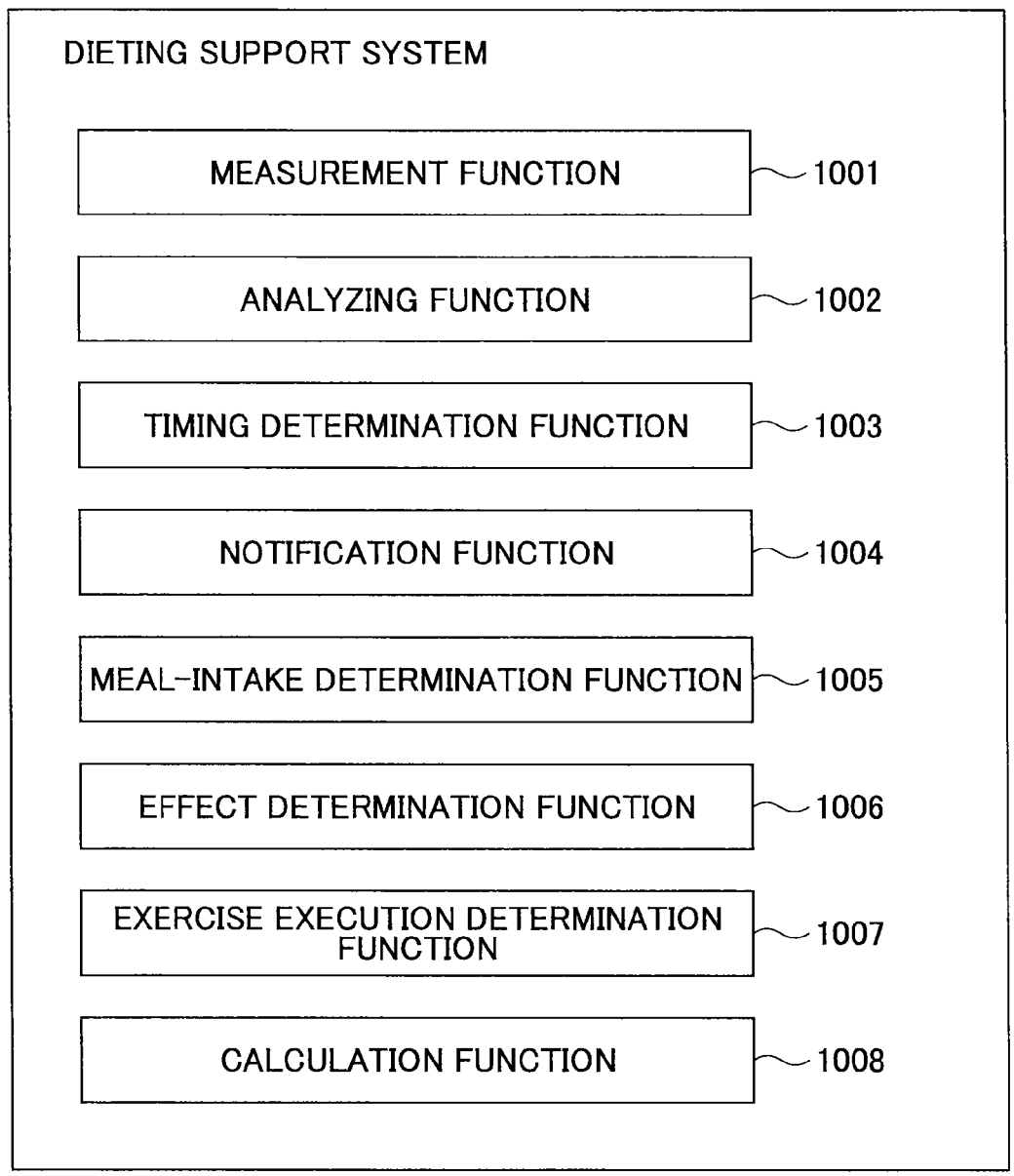
FIG. 10 is a functional block diagram showing functions of the dieting support system according to the embodiment of the present invention.

FIG. 10 is a functional block diagram showing functions of a dieting support system 1000 in the embodiment of the present invention. The dieting support system 1000 according to the embodiment of the present invention is characterized in that it includes a measurement function 1001 that detects components of biogas and that measures concentration of the biogas; an analyzing function 1002 for accumulating and analyzing the measurement result; and a timing determination function 1003 that determines timing which is suitable for taking a meal or timing which is suitable for doing exercise, depending on the analyzed result.

Here, the "biogas" means all gases discharged by a living body. The biogas includes various types of gases that are discharged outside through a respiratory tract (e.g., a lung, a bronchial tube, a nose, and a mouth), various types of gases discharged from a skin, and various types of gases discharged from mucous membrane. These biogases include both organic components and inorganic components. The organic components include, but are not limited to, a ketone such as acetone; an alcohol such as ethanol; an ester; a mercaptan such as methyl mercaptan; an olefin such as isoprene; and an amine. Further, the inorganic components include, but are not limited to, water, carbon monoxide, carbon dioxide, hydrogen sulfide, ammonia, nitric monoxide, and oxygen.

There are no particular restrictions for a method and a device for detection and concentration measurement of such components of the biogas. Various known detection and concentration measurement methods and devices can be selected and utilized. Here, the various known detection and concentration measurement methods conform to the types of the above-described biogas, and conform to a content (concentration) within an expected range of the above-described biogas. Usual components and their concentration which are discharged from the living body have been well known so far, and it is easy to select the method or the measure for the detection and concentration measurement of such components. In a method in the embodiment of the present invention, a selective semiconductor gas sensor can be used for the various biogas components, though it is not limited to this. Regarding such a sensor, various types of sensors have been put on the market. The sensors are usable as they are, or the sensors can be easily made usable by modifying and optimizing them by a generally known method.

There are no particular restrictions for the analyzing function 1002 for accumulating and analyzing the measurement result. The measurement result (measurement data, data for calibration, and other data (for comparison)) can be stored and accumulated, or the measurement result can be stored and accumulated with other information (e.g., environmental information such as time and location of the measurement, and personal information) by selecting a generally known method. The data can be read or overwritten, so that it is used for the analysis below.

There are no particular restrictions for the timing determination function 1003 that determines the timing which is suitable for taking the meal and the timing which is suitable for doing exercise based on the obtained measurement result. The analysis can be made based on the measured data and other information which has already been accumulated, such as electronic schedule data, a blog, and manually input data. A preferable timing determination method of the embodiment of the present invention is explained below.

There are no particular restrictions for the timing determination function 1003, which is one of the characteristics of the present invention, for determining the timing which is suitable for taking the meal or the timing which is suitable for doing exercise. It suffices if the timing determination function 1003 can determine the timing based on the determination obtained by the above-described result of the analysis. It is preferable that the reporting of the timing be made as soon as the determination is made. When the reporting is delayed, it is possible that the best timing is missed.

For the embodiment of the present invention, there are no particular restrictions for time of the detection of the biogas, a period of the detection of the biogas, and a number of times of the detection of the biogas components. Rather, a type of the component to be detected, the number of times of detection, and the detection period can be freely selected, so that they are adjusted to the user's individual difference (e.g., an objective, or a physical condition). For example, it is preferable to perform detection in advance for a certain period based on a constant schedule, so as to obtain basic information at an earlier stage, and that processing of the measured data and processing based on the data (e.g., statistical processing such as averaging and trend analysis) be performed for various daily states (e.g., a resting state, a physical activity state, a living active state, or a state of doing exercise). Further, it is preferable to accumulate measured results which have been detected and measured before, after, and during the meal; and before, after, and during the exercise, in accordance with the user's usual daily meal taking habit and exercise habit. By using these data which have been accumulated in advance, the precision of the analysis of the present invention is improved, and more suitable timing can be determined.

Further, the functions of the dieting support system 1000 according to the embodiment of the present invention can be executed while they are temporally and spatially separated, or some of or all of the functions can be executed while they are cooperating. For example, it is possible to configure the measurement function 1001 that detects the biogas components and that measures the concentration of the biogas components, the analyzing function 1002 that accumulates and analyzes the measured result, and a notification function 1004, so that they are executed by temporally and spatially separated devices. For such a case, it is preferable that the functions of the dieting support system 1000 according to the embodiment of the present invention further include a transmission and reception function that transmits and receives the measured result (additionally, other information which is related to the measured result) by using various measures/devices. Specifically, transmission and reception through a wired line, a wireless channel, or a network can be considered, though they are not limited to these. With such a configuration, the user can transmit the result which is detected and measured by the user to a device including the analyzing function 1002 that accumulates and analyzes the result and the notification function 1004 that reports the result through the wired line, the wireless channel, or the network. Additionally, the result of the analysis, the timing suitable for taking the meal, and the timing suitable for doing exercise can be reported to the user through the wired line, the wireless channel, or the network.

One of the embodiments of the dieting support system is characterized in that the biogas is acetone. It is known that acetone is included in the biogas, and that presence, concentration, and a concentration change of acetone indicate a reaction in a living body, especially a fat-burning condition. Further, in such a case, the analyzing function 1002 includes the timing determination function 1003 that determines whether it is the timing suitable for taking the meal, or that determines whether it is the timing suitable for doing exercise, by comparing the measurement result of the acetone concentration with a predetermined threshold value, or by comparing the measurement result of the acetone concentration with a result of accumulated acetone concentration that was measured in the past. The detection and concentration measurement of acetone is explained above. Further, the predetermined threshold value is a value which is unique to the user and which is derived from the acetone concentration that is measured under a basic condition in a certain period (during, before, and after the meal; during, before, and after the exercise; and a living activity without exercise) and accumulated. The predetermined threshold value is a value with which the determination as to whether it is the timing which is suitable for taking the meal, or as to whether it is the timing which is suitable for doing the exercise is made. Namely, the threshold value is a value unique to the user, and the threshold value is a value which changes in accordance with a change of a subsequent state of the user (e.g., a change in the body weight, or a change in a fat-burning property). The threshold value may be defined by the user, or the threshold value may be defined by a third party such as a physician who is guiding the dieting.

Another one of the embodiments of the dieting support system is the above-explained dieting support system 1000, and it is characterized in that it further includes a meal-intake determination function 1005 that determines whether the meal is taken within a predetermined time interval. When a determination is made, as a result of the analysis, that it is the suitable timing for taking the meal, or that it is the suitable timing for doing exercise, and when a determination is made, by this function, that the meal is not taken within the predetermined time interval, a message is transmitted which prompts the user to take the meal; and when the determination is made, as the result of the analysis, that it is the suitable timing for taking the meal, or that it is the suitable timing for doing exercise, and when a determination is made, by this function, that the meal is taken within the predetermined time interval, a message is transmitted which prompts the user to do the exercise. In the present invention, there are no particular restrictions for the "predetermined time interval." It is a value which is unique to the individual user, and which is determined by the user's dietary habit. Usually, it is input by the user, and the data is accumulated for the subsequent analysis/determination. For example, when three meals of breakfast, lunch, and dinner are taken at 6:00 a.m., 12:00 p.m., and 6:00 p.m., respectively, the time intervals are 6 hours, 6 hours, and 12 hours, respectively. Further, in the embodiments of the present invention, there are no particular restrictions regarding the method of determining whether the meal is taken, the determination may be made based on input information of the user. The embodiments of the present invention also include determining by another method when it is unknown whether the user takes the meal.

Another embodiment of the dieting support system is characterized in that the above-explained meal-intake determination function 1005 detects a rise of concentration of one or more gas components of ethanol, methyl mercaptan, and hydrogen sulfide, which are discharged from a living body; refers to the electronic schedule data; refers to the blog or the manually input data; or performs a combination of these. Here, ethanol, methyl mercaptan, and hydrogen sulfide, which are discharged from the living body, are for exemplifying the gas that is discharged as a result of a reaction that occurs in the living body by taking the meal. The present invention is not limited to these. Since the types of the gas components may vary depending on a dietary constituent, a component other than these gas components may be included. The manually input data is explained above. Further, for the electronic schedule data, schedule data that has been determined by the user in advance can be digitized and accumulated.

Another embodiment of the dieting support system is characterized in that it further includes an effect determination function 1006 that determines whether there is an effect of the exercise which was done in the past. When it is determined that there is an effect of the exercise, a message is transmitted to the user which recommends doing exercise at exercise intensity and for an exercise time period which are the same as those of the previous time. When it is determined that there are no effects of the exercise, a message is transmitted which recommends doing exercise while increasing the exercise intensity greater than that of the previous time or extending the exercise time period greater than that of the previous time. Here, the "effect of the exercise that was performed in the past" in the embodiment of the present invention means an effect of the exercise that occurs as the dieting effect. Accordingly, in the embodiment of the present invention, there are no particular restrictions regarding the "effect of the exercise that was performed in the past." It suffices if it is an index with which the effect can be compared with that of the exercise currently done, based on various quantitative indexes, semi-quantitative indexes, and qualitative indexes. Further, there are no particular restrictions regarding the exercise intensity, provided that the exercise intensity means intensity of the exercise. However, it is preferable to use values (e.g., a metabolic equivalent (MET) value) that can be quantitatively handled, and that are concretely well-known for various types of exercise (activities). Further, when the MET value is adopted as the exercise intensity, the value obtained by being multiplied by the exercise time period is regarded as a quantity of the exercise (or the exercise). Thus, for determining the effect of the exercise which was done in the past, the determination can be made by comparing it with the same quantity of the exercise which was done in the past (for which (the MET value)×(the exercise time period) is the same value, for example).

Another embodiment of the dieting support system is characterized in that the above-explained effect determination function 1006, which determines whether there is the effect of the exercise which was done in the past, is based on whether a total amount or an average value of acetone during a predetermined time period after the exercise which was done in the past is increased compared to a total amount or an average value of acetone during a predetermined time period prior to the exercise which was done in the past. As explained above, preferably, in the embodiment of the present invention, the user performs detection and measurement of the biogas, which is acetone, in advance for a certain time period, continuously and periodically, and the user accumulates the measurement data with other information. Based on such accumulated data of acetone, a determination can be made as to whether the total amount or the average value of acetone is altered or increased by doing specific exercises. The increase in the total amount or in the average value of acetone indicates that the user's fat-burning condition is improved.

Another embodiment of the dieting support system is characterized in that it further includes an exercise execution determination function 1007 that determines whether exercise is done within the predetermined time interval, and that it transmits a message to the user which recommends doing exercise when the determination is made that the exercise is not done. Here, the "predetermined time interval" is a value which is unique to the user. It is a time interval which is input in advance by the user by deciding the time interval for doing the exercise, or it is a value which is recommended in advance as the time interval for doing the exercise. The determination as to whether the exercise is done may be made by manual inputting by the user. Alternatively, when it is unknown to the user, the determination as to whether the exercise is done may be made by another method. There are no particular restrictions for the other method. However, it is made possible by measuring a change in the components of the biogas or a change in the concentration of the components, which occurs for a case where the exercise is done within a certain time interval.

Another embodiment of the dieting support system is characterized in that the exercise execution determination function 1007 that determines whether the exercise is done is based on any of or a combination of detecting a rapid increase in the concentration of acetone or isoprene which is discharged from the living body within a predetermined time period; referring to data of a pedometer; referring to data of an active mass meter; referring to the electronic schedule data; and referring to the blog or the manually input data. Here, the explanation is given above regarding referring to the input by the user or the schedule data which is digitized in advance. In the embodiment of the present invention, preferably, the determination as to whether the exercise is done may be made by detecting the biogas, apart from user's own consciousness. There are no particular restrictions for the change of the components of the biogas or the change of the concentration of the components which occur when the exercise is done within the certain time period. However, it may be biogas which is produced as a result of doing the exercise and burning glucose and fat, which are energy sources in the living body. In the embodiment of the present invention, it is especially preferable to detect the rapid increase in the concentration of acetone or isoprene as the components of the biogas. Further, besides the detection of the biogas, other exercise indexes can be considered, such as referring to the data of the pedometer or the data of the active mass meter. These data may be input by the user or automatically detected in association with the exercise, and these data may be transmitted to the exercise execution determination function 1007 by the user or automatically.

Another embodiment of the dieting support system is the dieting support system 1000 which is characterized in that it further includes a calculation function 1008 that calculates the fat-burning condition in a predetermined time period from the total amount of acetone in the predetermined time period, and that it reports the calculated result. Here, the predetermined time period is a value which is unique to the user. It can be suitably determined depending on an object of supporting the dieting, for example, by a number of times of detecting acetone in the time period, so as to calculate the fat-burning condition within the time period. For example, for a case where the fat-burning condition is changed by taking the meal, it is preferable to perform the detection and the measurement of acetone at least twice, namely, prior to and after the meal. Further, for a case where it is changed by doing the exercise, it is preferable to perform the detection and the measurement of acetone at least twice, namely, prior to and after the exercise. Further, for a case where the fat-burning condition of the whole day is to be calculated, it is preferable to perform the detection and the measurement of acetone at least twice in accordance with a normal daily activity (including the meal and the exercise). Similarly, for a case where the fat-burning condition is calculated for a long time of one or more days, it is preferable to perform the detection and the measurement of acetone several times over a period of several days, several weeks, or longer, and to accumulate data. Further, for the calculation of the fat-burning condition, burning of the fat can be directly calculated from the measured value of the concentration of acetone by using a suitable known biochemical reaction formula. Additionally, it can be indirectly calculated by obtaining a correlation with the fat-burning condition by a relative value of the measured value of the concentration of acetone or a tendency analysis of the measured value of the concentration of acetone. Further, the calculation method of the fat-burning condition is also explained in an embodiment 7—quantification methods of a fat burning condition and a quantity of exercise. Further, since such a fat-burning condition includes a value and a tendency which are unique to the user, it can be a very effective value for supporting the dieting of the user, such as taking the meal, doing the exercise, and changing the daily activity.

Another embodiment of the dieting support system is the dieting support system 1000 which is characterized in that the components of the biogas are discharged from one or more of breath, skin, and a mucous membrane; the components of the biogas are at least one of selected from a group including acetone, ethanol, methyl mercaptan, hydrogen sulfide, isoprene, nitric monoxide, oxygen, and carbon dioxide; and the measurement function 1001 that detects the components of the biogas and that measures the concentration of the biogas detects and measures them at every predetermined time interval or at any timing by utilizing one or more sensors.

(Terminal Device)

Figure 11:
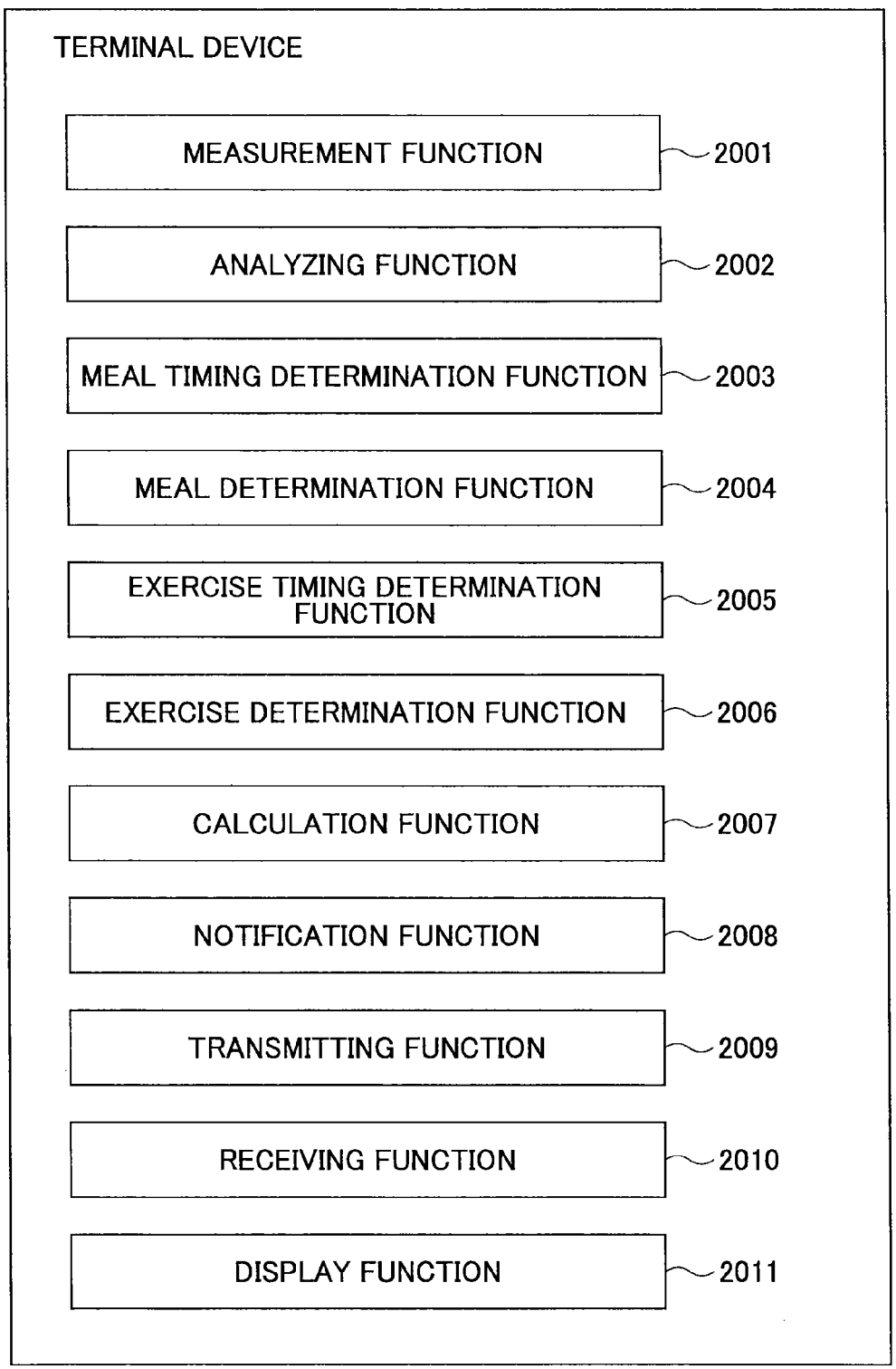
FIG. 11 is a functional block diagram showing functions of the terminal device according to the embodiment of the present invention.

FIG. 11 is a functional block diagram showing functions of the terminal device 2000 in the embodiment of the present invention. The embodiment of the present invention provides the terminal device 2000 which is characterized in that it includes a measurement function 2001 that detects the biogas discharged from the living body and that measures its concentration; a transmitting function 2009 that transmits the measured result to outside; and a receiving function 2010 that receives a message regarding the suitable timing for taking the meal or doing the exercise; the recommended meal, exercise, or lifestyle; or the fat-burning condition. The terminal device 2000 is one concrete device for implementing the dieting support system 1000 in the embodiments of the present invention which are explained above. Here, the measurement function 2001 that detects the biogas discharged from the living body and that detects its concentration is already explained. Further, there are no particular restrictions for the transmitting function 2009, and it includes all functions for communicating the usual data of the measured result, and measures for materializing them. For example, transmissions through a wired line, a wireless channel, or a network can be considered. For the embodiment of the present invention, the transmission through the network is particularly preferable. Further, there are no particular restrictions for the receiving function 2010 that receives the message regarding the suitable timing for taking the meal or doing the exercise; the recommended meal, exercise, or lifestyle; or the fat-burning condition. For example, reception from the outside through the wired line, the wireless channel, or the network can be considered. For the embodiment of the present invention, the reception through the network is especially preferable. Further, depending on a case, a display function 2011 may be included which displays and announces the received message in various methods. For example, an announcement by a sound, or a display function by a display device can be considered. The message regarding the recommended meal includes, for example, information regarding a menu, a quantity, a number of times, a number of calories, and a distribution ratio of carbohydrates of the meal. The message regarding the recommended exercise includes, for example, information regarding a type, intensity, a time period, and a number of times of the exercise to be done. Further, the message regarding the recommended lifestyle includes, for example, information that recommends refrain from snacking and midnight snacking, using a stairway, and getting off a train at one station prior to the nearest station and taking a walk.

Another embodiment of the terminal device is characterized in that it further includes an analyzing function 2002 that accumulates and analyzes the measured result of the detected biogas; a meal timing determination function 2003 that determines the suitable timing for taking the meal; a meal determination function 2004 that determines information regarding the recommended meal; an exercise timing determination function 2005 that determines the suitable timing for doing the exercise; an exercise determination function 2006 that determines the intensity and the time period of the exercise to be done; a calculation function 2007 for calculating the fat-burning condition; and a notification function 2008 that sends the message regarding the suitable timing for taking the meal or doing exercise, the information about the recommended meal, the intensity and the time period of the exercise to be done, or the fat-burning condition. The terminal device 2000 in the embodiment of the present invention is the above-explained terminal device including the analyzing function 2002 that accumulates and analyzes the measured result of the detected biogas; the meal timing determination function 2003 that determines the suitable timing for taking the meal; the meal determination function 2004 that determines information regarding the recommended meal; the exercise timing determination function 2005 that determines the suitable timing for doing the exercise; the exercise determination function 2006 that determines the intensity and the time period of the exercise to be done; the calculation function 2007 for calculating the fat-burning condition; and the notification function 2008 that sends the message regarding the suitable timing for taking the meal or doing exercise, the information about the recommended meal, the intensity and the time period of the exercise to be done, or the fat-burning condition. Thus, the terminal device can independently achieve the dieting support system in the embodiment of the present invention that is explained so far, without requiring transmission to and reception from outside.

(Server)

Figure 12:
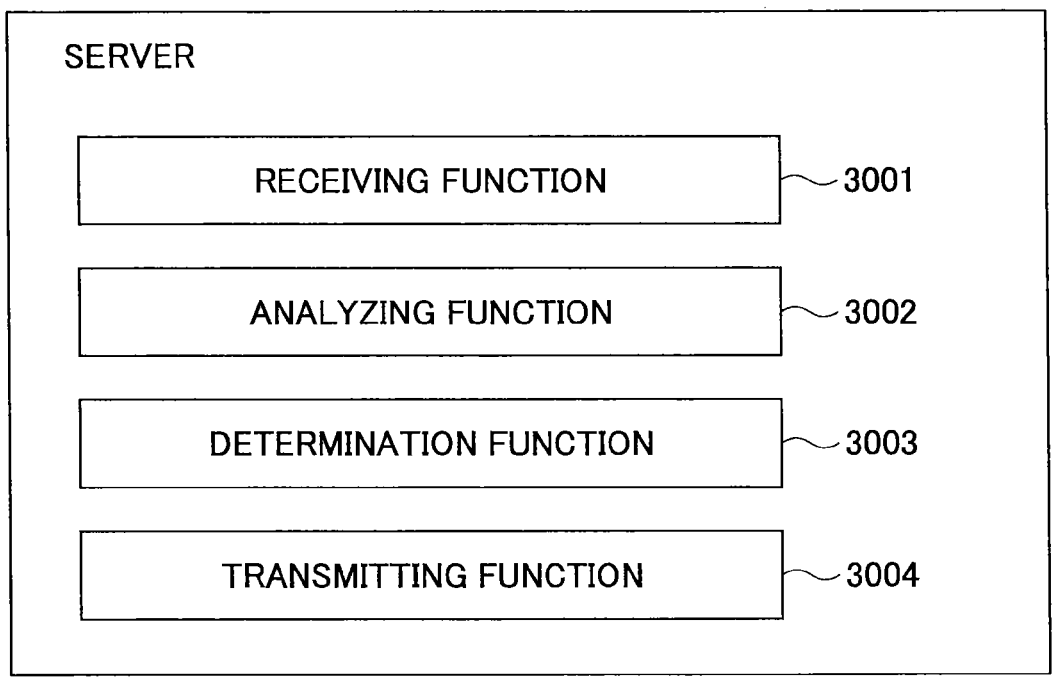
FIG. 12 is a functional block diagram showing functions of the server according to the embodiment of the present invention.

FIG. 12 is a functional block diagram showing functions of a server 3000 in the embodiment of the present invention. The embodiment of the present invention provides the server 3000 which is characterized in that it includes a receiving function 3001 that receives the measured result of the biogas which is discharged from the living body; an analyzing function 3002 that accumulates and analyzes the measured result of the biogas which is received; a determination function 3003 that determines the suitable timing for taking the meal or the suitable timing for doing the exercise, the recommended meal, exercise, or lifestyle, or the fat-burning condition; and a transmitting function 3004 that transmits the message regarding the suitable timing for taking the meal or doing the exercise, the recommended meal, exercise, or lifestyle, or the fat-burning condition. The server 3000 is the above-explained server including the receiving function 3001 that receives the measured result of the biogas which is discharged from the living body; the analyzing function 3002 that accumulates and analyzes the measured result of the biogas which is received; the determination function 3003 that determines the suitable timing for taking the meal or the suitable timing for doing the exercise, the recommended meal, exercise, or lifestyle, or the fat-burning condition; and the transmitting function 3004 that transmits the message regarding the suitable timing for taking the meal or doing the exercise, the recommended meal, exercise, or lifestyle, or the fat-burning condition. When the server 3000 is combined with the above-explained terminal device 2000 in the embodiment of the present invention, the server 3000 can achieve the dieting support system 1000 in the embodiment of the present invention. There are no particular restrictions for a transmission and reception method between the server 3000 and the terminal device 2000. For example, transmission and reception through a wired line, a wireless channel, or a network may be considered. In the embodiment of the present invention, the transmission and reception through the network are especially preferable.

(Dieting Support Method)

Further, according to the embodiment of the present invention, there is provided a dieting support method which is characterized in that it executes a step of detecting the biogas components which are discharged from the living body and measuring their concentration; a step of accumulating and analyzing the measured result; and a step of reporting, depending on the analyzed result, the timing suitable for taking the meal or doing the exercise, the recommended meal, exercise, or lifestyle, or the fat-burning condition. Here, the steps are concretely explained above. The steps may be executed by a human, or a computer. For the case of the human, it may be the user; medical personnel such as a physician, a nurse, or a technician; or a supplier that provides the dieting support method and the system.

Further, the embodiment of the present invention includes the dieting support system and the dieting support method which are explained so far, and which are characterized in that they include the terminal device 2000; the network; and the server 3000 that communicates with the terminal device 2000 through the network. The terminal device 2000 includes the measurement function 2001 that detects the biogas and that measures the concentration of the biogas; the transmitting function 2009 that transmits the measured result from the terminal device to the server through the network; the receiving function 2010 that receives the message from the server 3000 through the network; and the display function 2011 that displays the message which is received from the server 3000. The server 3000 includes the receiving function 3001 that receives the transmitted measured result; the analyzing function 3002 that accumulates and analyzes the received measured result; the determination function 3003 that determines whether it is the suitable timing for taking the meal or whether it is the suitable timing for doing the exercise by comparing the measured result of the concentration of the biogas with the predetermined threshold value or by comparing the measured result of the concentration of the biogas with the result of accumulating the acetone concentration that was measured in the past; and the transmitting function 3004 that transmits the message which recommends taking the meal or the message which recommends doing the exercise to the terminal device 2000 through the network.

Hereinafter, the embodiments of the present invention are explained further in detail by using the accompanying drawing as well as the exemplifying embodiments. However, the present invention is not limited to these embodiments.

Embodiment 1

An Example of Terminal-Network-Server

Figure 1:
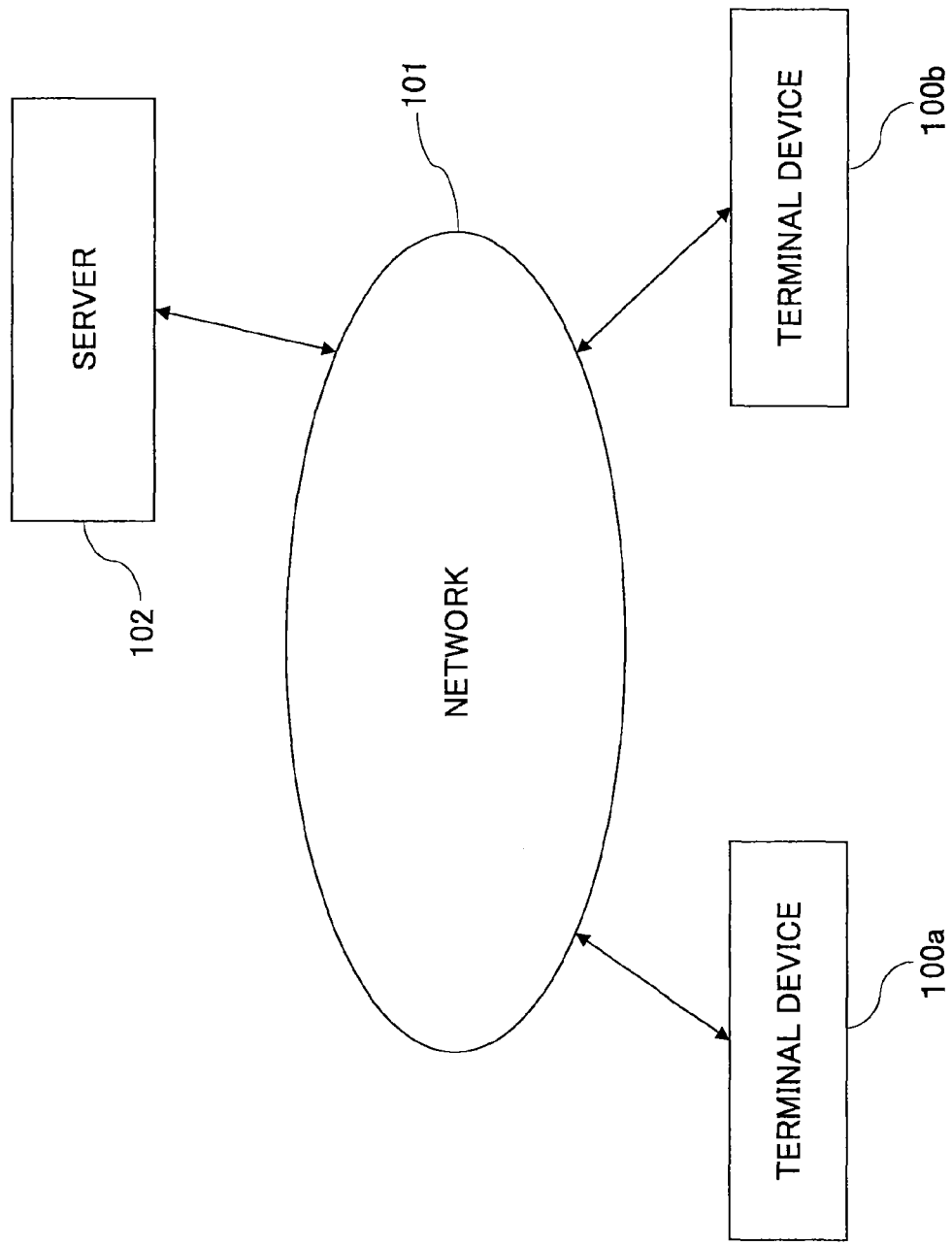
FIG. 1 is an example of a configuration of a dieting support system according to an embodiment of the present invention.

FIG. 1 shows an example of a system configuration according to one embodiment of the present invention. The configuration is such that terminal devices 100a, 100b, and a server 102 can transmit and receive (hereinafter, which may also be referred to as "communication") through a network 101. Here, two terminal devices are shown for an exemplifying purpose. However, it may be one terminal device, at least.

Here, the terminal devices 100a and 100b are terminal devices which are owned (used) by the user of the system. For example, the terminal devices 100a and 100b include portable or wearable electronic devices, such as a mobile telephone, a smart phone, a PDA, and various sensor devices. Further, another example of the system configuration is such that, for example, the terminal devices 100a and 100b are the sensor devices that communicate with the portable telephone, the smart phone, the PDA, or the like by using near field communications such as a wireless LAN, Bluetooth, or ZigBee, and the mobile phone, the smart phone, the PDA, or the like can communicate with the server through the network 101.

Figure 2:
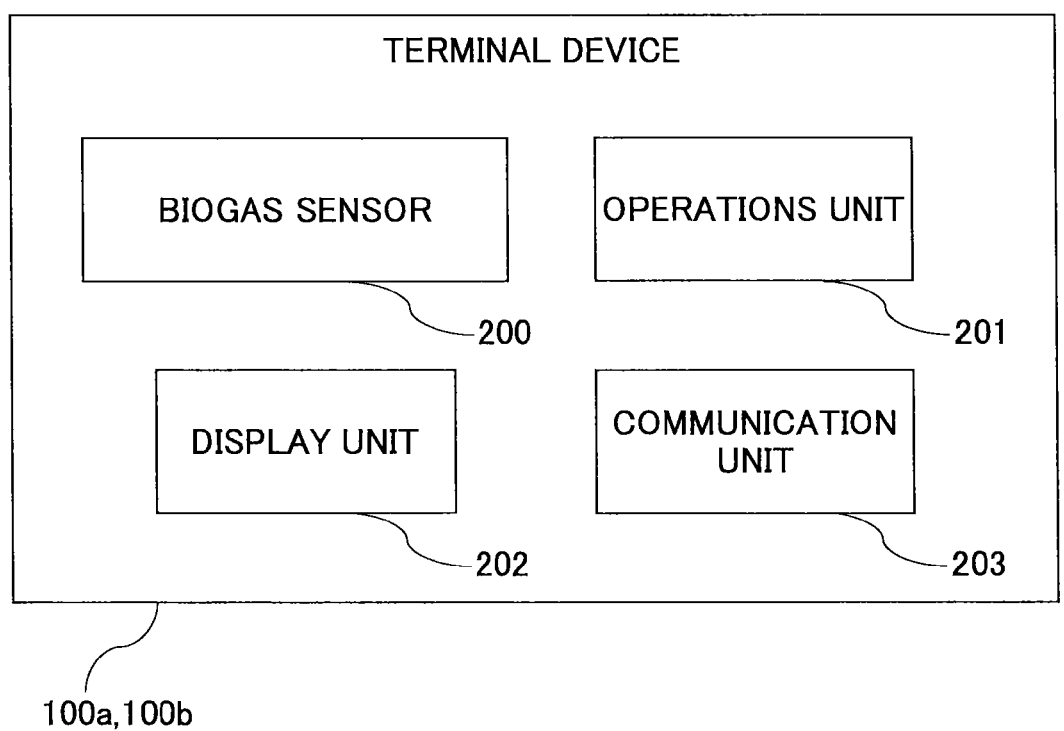
FIG. 2 is an example of a configuration of a terminal device according to the embodiment of the present invention.

As shown in FIG. 2, each of the terminal devices 100a and 100b includes a biogas sensor 200, and each of the terminal devices 100a and 100b measures concentration of at least one gas component among acetone, ethanol, methyl mercaptan, hydrogen sulfide, isoprene, nitric monoxide, oxygen, and carbon dioxide, which are included in the gas (the biogas) discharged from the living body of the user periodically or at a certain timing, by using one or more sensors. The measurement can be performed by the user, for example, by breathing on the biogas sensor 200 of the terminal device. Further, for the case where the terminal devices 100a and 100b are the mobile phones, the biogas can be collected during calling by the biogas sensor 200.

Each of the terminal devices 100a and 100b may further include a communication unit 203 that can communicate with the network, and the terminal devices 100a and 100b transmit the measured data from the biogas sensor or other information (e.g., user's personal information, or manually input information) to the server. The communication unit has a configuration to receive a message and other information which are transmitted from the server. Each of the terminal devices 100a and 100b may further include a display unit 202, where the display unit 202 has a configuration to display functions of the terminal device (a menu), information which is manually input by the user, transmission data for the server, and received data/information from the server for visual confirmation. Specifically, a liquid crystal display device may be considered. Each of the terminal devices 100a and 100b may further include an operations unit 201 for controlling the above-described functions (e.g., the biogas sensor 200, the display unit 202, and the communication unit 203). Such control includes, for example, displaying, by the operations unit 201, predetermined time (the date and time) and a time interval on the display unit 202 so as to confirm and prompt the measurement of the biogas to the user; confirming and prompting the timing for manually inputting the personal information (e.g., the result of the measurement of the body weight, and the result of doing the exercise), which is necessary for the user, or the environmental information (e.g., the outside air temperature, and the humidity); transmitting (which includes prompting to the user or automatic transmission) the data and information to the server at a predetermined timing; and inquiring from the user to the server (e.g., a request for transmission of the analyzed/determined result, browsing of the content of the accumulated data, or correcting/modifying the data). Further, it includes control of contents and timing of the user's response to a message from the server (e.g., for the message for taking the meal, the meal is taken, and subsequently it is transmitted to the server). The operations unit 201 may be integrally formed with the display unit 202. For example, the user is allowed to select the functions by arranging the menu indicating the functions of the operations unit 201 on the display unit 202.

Figure 3:
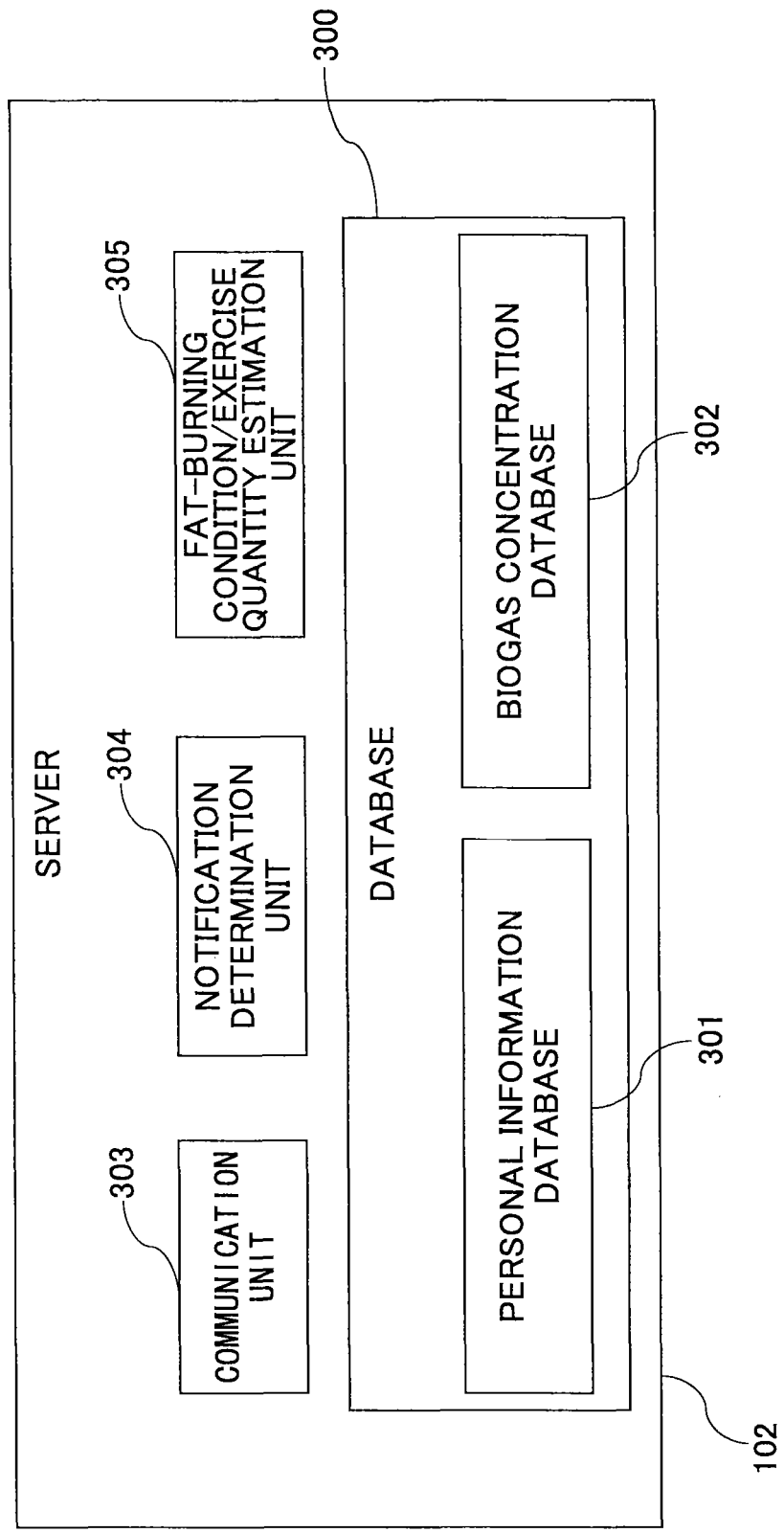
FIG. 3 is an example of a configuration of a server according to the embodiment of the present invention.

FIG. 3 shows an example of the server. Here, the server 102 includes a database 300 and a notification determination unit 304. The server 102 may further include a fat-burning condition/exercise quantity estimation unit 305 or a communication unit 303.

The database 300 includes a biogas concentration database 302 that accumulates the concentration of the biogas measured by the biogas sensor 200 together with the measured time information. FIG. 4 shows an example of the biogas concentration database 302. In the biogas concentration database 302 shown in FIG. 4, the information regarding the time of the measurement, the types of the measured components (here, which are acetone and ethanol), and the measured concentration (here, which is expressed in the unit of ppb) are listed together with the time.

The database 300 may also include a personal information database 301 that includes the personal information of the user and other information. FIG. 5 shows an example of it. Here, the user names, the genders, the body fat percentages, and the body mass indexes (BMI) of the users who own the terminal devices 100a and 100b are listed.

The notification determination unit 304 determines the timing suitable for taking the meal, the timing suitable for doing the exercise, the recommended meal, exercise, and lifestyle, based on the information of the database 300, and determines whether to report them to the user. The fat-burning condition/exercise quantity estimation unit 305 estimates the fat-burning condition and the quantity of the exercise of the user, based on the concentration information of acetone in the biogas concentration database 302. The estimation method is explained in the above-described example and in the embodiment 7—quantification methods of a fat burning condition and a quantity of exercise. However, the method of estimating the fat-burning condition and the quantity of the exercise of the user is not limited to these.

Embodiment 2

An Example 1 of Operations of the Dieting Support System

Figure 6:
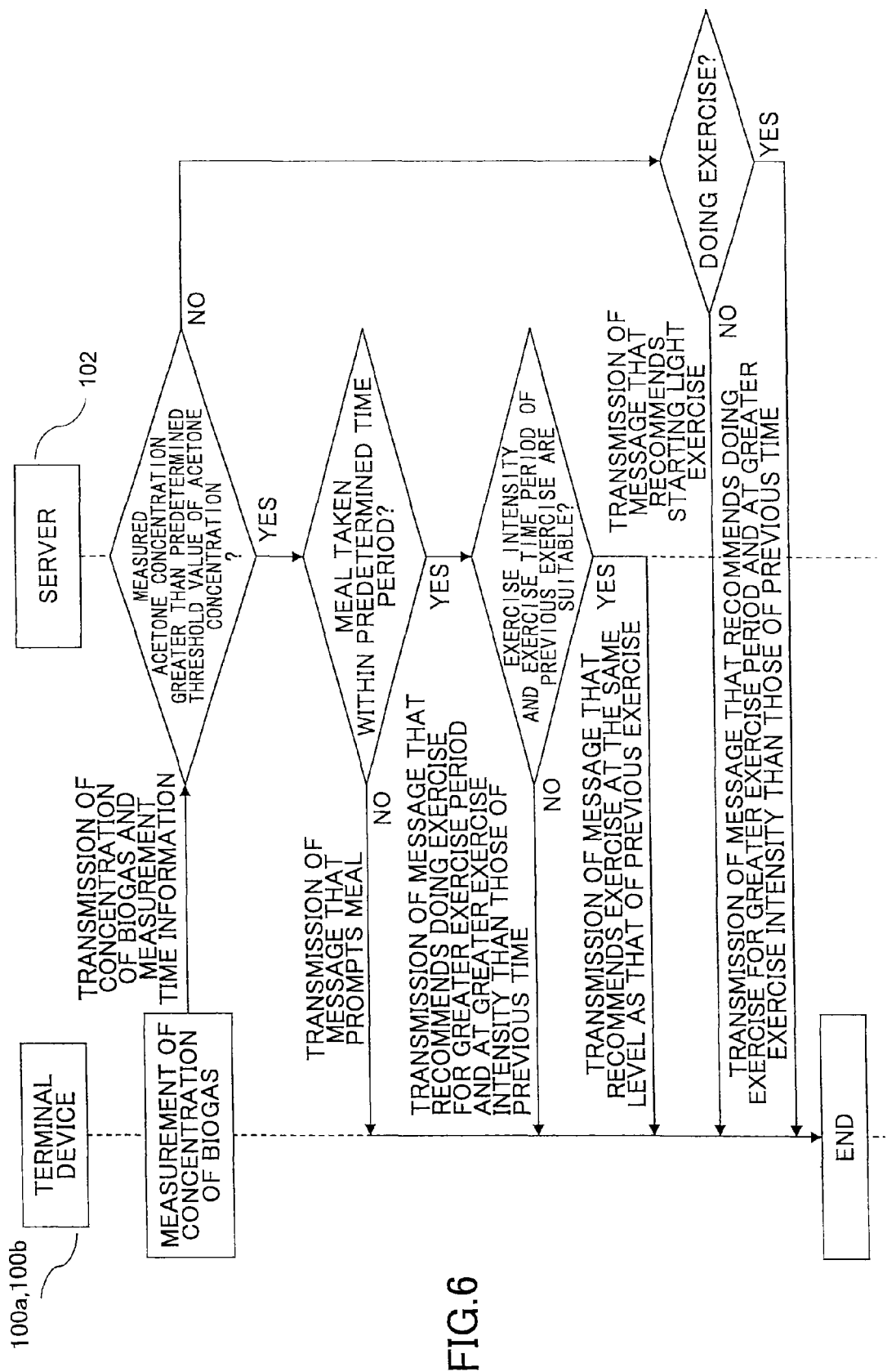
FIG. 6 is a flowchart showing an example 1 of operations of the dieting support system according to the embodiment of the present invention.

An example of operations is explained while referring to FIG. 6.

The concentration data and the measured time of the biogas, which is measured by the biogas sensor 200, are transmitted from the communication unit 203 to the server 102 through the network 101. A determination is made as to whether the measured concentration of acetone is greater than or smaller than a predetermined threshold value of the concentration of acetone, based on the biogas concentration database 302 which is recorded in the server 102. As the threshold value, a value can be utilized such that it is calculated from the concentration of acetone from which the fat is expected to start burning (for example, it is 37 nmol/l=0.83 ppm in Clin. Chem., 39/1, 87-92, 1993) by referring to the acetone concentration immediately after waking up on the date of the measurement of the biogas, an average value of the acetone concentration immediately after waking up which is derived from the acetone concentration that has been recorded, an average value of the acetone concentration from which fat of a person starts burning, whose BMI and value of the body fat percentage are close to those of the user who measures the concentration of acetone, or a document.

Figure 9:
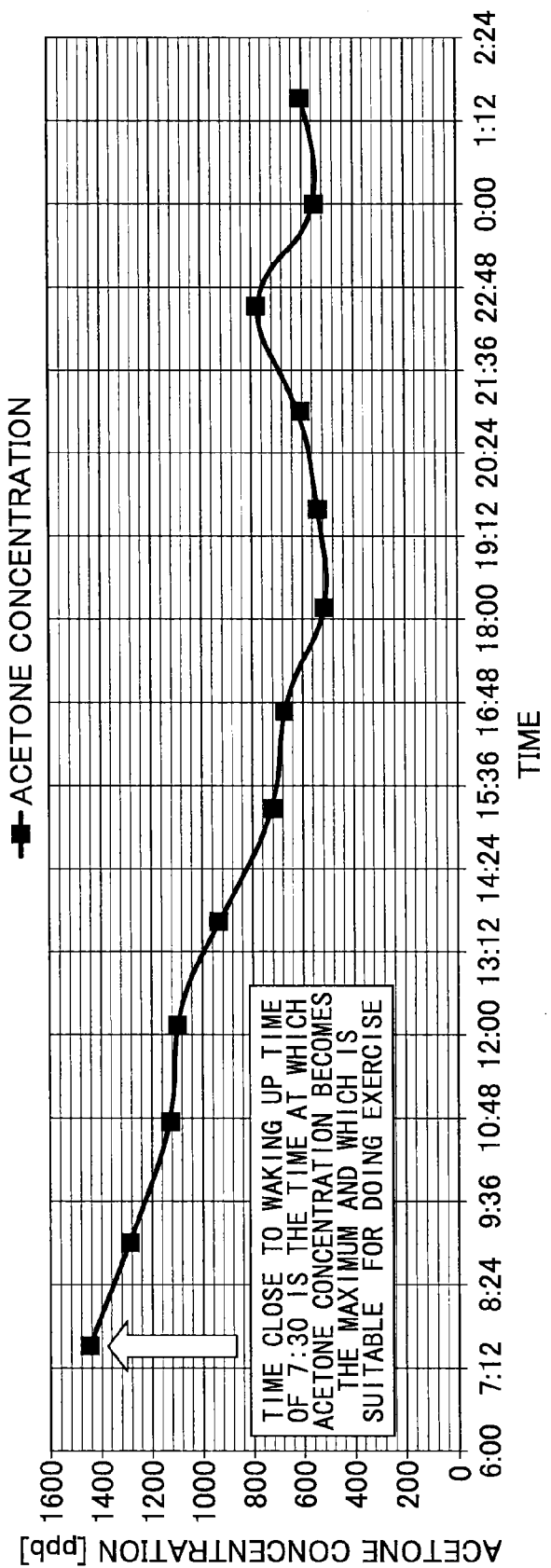
FIG. 9 shows an example of a graph which is calculated during operations of an example 3 of the dieting support system according to the present invention.

Especially, since the concentration of acetone immediately after waking up is usually the concentration of acetone in a state where the meal is not taken for greater than or equal to six hours, it can be regarded as a reference value for the concentration of acetone during fasting. However, it is not limited to this, and any concentration can be set as the threshold value depending on the circumstance of the measurement. For example, a graph may be derived by averaging fluctuation in the day of the concentration of acetone of the user in a predetermined time period such as shown in FIG. 9, and it may be set as an object to be compared with.

(I) A Case where the Measured Concentration of Acetone is Greater than the Predetermined Threshold Value of the Concentration of Acetone It is determined whether the meal is taken in a predetermined time period. As a method of determining whether the meal is taken, there is the method below, for example. It has been empirically known that concentration of ethanol in breathing gas is slightly increased temporarily after taking the meal. Thus, an increase in the concentration of ethanol in the breathing gas can be used for determining whether the meal is taken. However, the determination of whether the user takes the meal is not limited to the method of utilizing the concentration of ethanol in the breathing gas. For example, after taking the meal, concentration of components of an oral odor such as methyl mercaptan or hydrogen sulfide tends to increase. Thus, an increase in the concentration of the components of the oral odor may be used for determining whether the meal is taken. Further, it has been known that water soluble components in drinking water are discharged roughly as perspiration. Thus, a determination as to whether the meal is taken may be made based on an increase in a discharge amount of a specific component in the perspiration. The user may input whether the meal is taken to the terminal devices 100a and 100b. Information regarding the meal may be retrieved from an electronic schedule book or a blog of the user. Alternatively, for the user who takes the meal at almost fixed time, the time for taking the meal may be input in advance.

(i) A Case where the Meal is Taken within a Predetermined Time Period

A determination is made that it is in a state where body fat is easily burned, if exercise is done. Subsequently, it is determined whether the exercise intensity and the exercise time period of the exercise, which was done previous time, are suitable. As the determination method, that of the embodiment 7—quantification methods of a fat burning condition and a quantity of exercise—is utilized (which is described later). The quantity of exercise in a predetermined time period during which no exercise is done is compared with the quantity of the exercise in the predetermined time period where the previous exercise was done. When the quantity of the exercise in the predetermined time period for the case where the previous exercise was done is greater by a certain amount, it is determined that the effect of the exercise is obtained, and a message that recommends doing the exercise is transmitted, where the level of the exercise is the same as that of the previous exercise. When it is not greater by the certain amount, the effect of the exercise is not obtained. Accordingly, a message that recommends doing the exercise is transmitted, where the exercise time period is longer or the exercise intensity is greater than that of the previous time. As an index of the exercise intensity, for example, a Metabolic Equivalent (MET) is known. For example, for a case where running was done for thirty minutes at 8.4 km/hour (9.0 METs), but it is determined that the quantity of the exercise is insufficient, a message is transmitted that recommends doing running at 10.8 km/hour (11.0 METs) for forty minutes. Here, the index of the exercise intensity is not limited to the MET, and the exercise intensity may be derived from an oxygen intake or a heart rate, for example.

(ii) A Case where the Meal is not Taken within the Predetermined Time Period

It is a state where the body fat is easily burned, if the exercise is done. However, it is determined that the meal is not taken for a long time. Accordingly, a message that prompts to take the meal is transmitted to the user, so as to prevent excessive dieting. This message may include information regarding the meal, which is recommended for dieting. For a case where the measured concentration of acetone is significantly greater than a predetermined threshold value of the concentration of acetone, it is assumed that it is a state where the decomposition of the body fat is considerably promoted, namely, it is assumed that it is a state where sugar content in the body is considerably small. Accordingly, a meal is recommended such that, for example, it has calories which are the same as suitable calories for one meal or which are greater than the suitable calories for the one meal by several hundreds kilocalories, and its distribution ratio of carbohydrates is greater (more than or equal to 70%) than the generally recommended distribution ratio. Here, the suitable calories for one meal are derived from the recommended daily intake of calories, which is calculated, for example, by the standard body weight (height (meters)×height (meters)×22 (BMI standard value))×the number of calories which is necessary for body weight of 1 kg (25-30 kilocalories). For a case where the measured concentration of acetone is approximately equal to the predetermined threshold value of the concentration of acetone, it is assumed that a state is suitable for dieting, where the decomposition of the body fat is maintained. Accordingly, a meal is recommended such that, for example, it has the same number of calories as the suitable number of calories for one meal which is derived from the recommended daily intake of calories or it has the number of calories which is less than the suitable number of calories for the one meal by several hundred kilocalories, and its distribution ratio of carbohydrates is the same as that of a normal meal (50-70%) or less than the normally recommended distribution rate (less than or equal to 50%).

(II) A Case where the Measured Concentration of Acetone is Less than the Predetermined Threshold Value of Acetone A determination is made that it is a state where the fat is not burning, that is, a state where the fat is not easily burned, even if exercise is done. It is determined whether the user does exercise so far. As a determination method, for example, an acceleration sensor; a pedometer; an active mass meter; an increase in concentration of carbon dioxide in breath; an increase in concentration of isoprene in the breath; an increase in a perspiration amount; inputting, by the user, of whether the exercise is done to the terminal devices 100a and 100b; or retrieving information regarding the exercise from the user's electronic schedule book or blog, may be utilized.

(i) A Case where it is Determined that the Exercise has been Done

A determination is made that the quantity of the exercise which is done by the user is insufficient. A message is transmitted which recommends the exercise, where the exercise intensity is greater and the exercise time period is greater.

(ii) A Case where it is Determined that the Exercise has not been Done

A message is transmitted which recommends starting light exercise.

Embodiment 3

An Example 2 of Operations of the Dieting Support System

Figure 7:
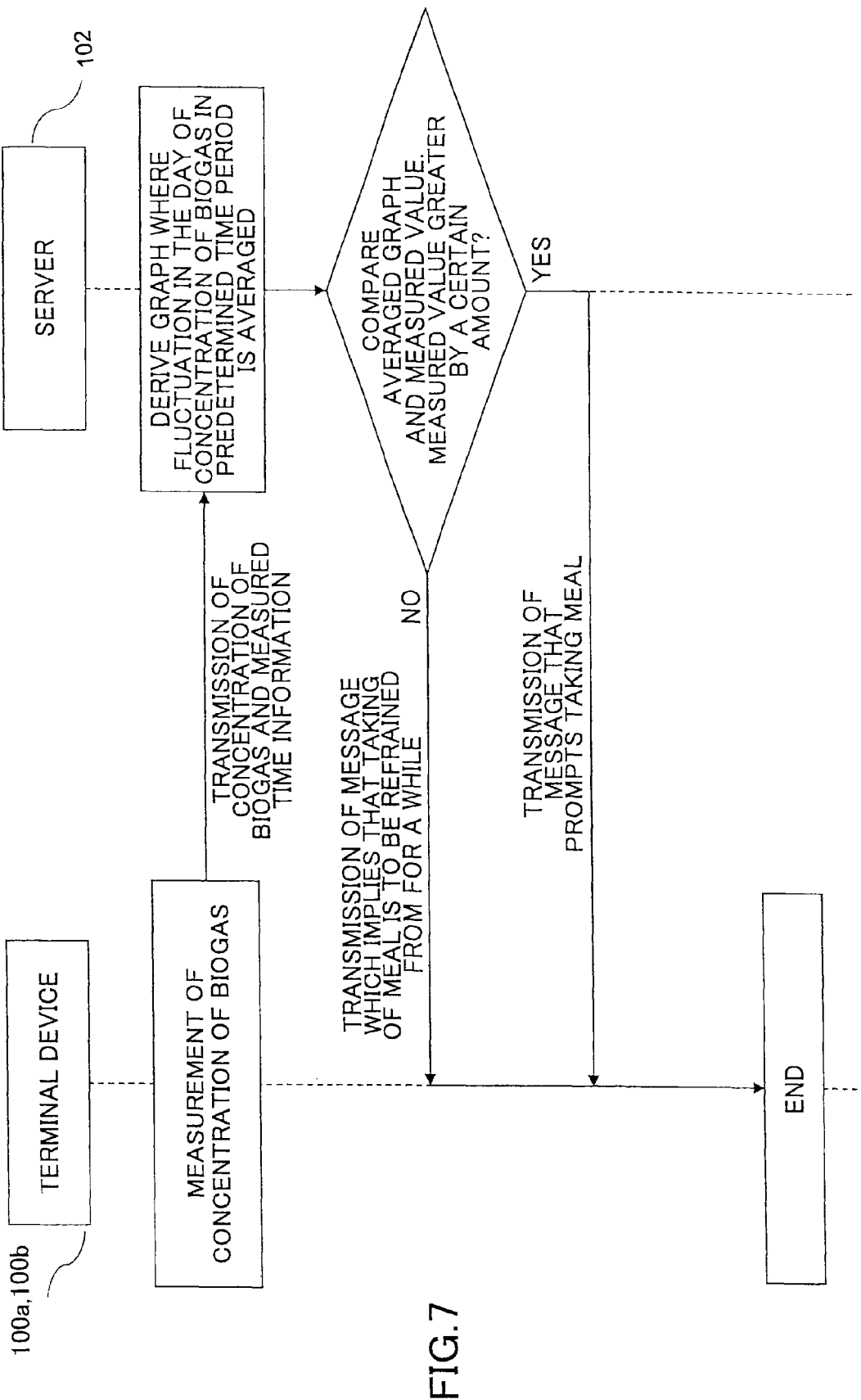
FIG. 7 is a flowchart showing an example 2 of operations of the dieting support system according to the embodiment of the present invention.

An example of operations is explained while referring to FIG. 7.

Figure 8:
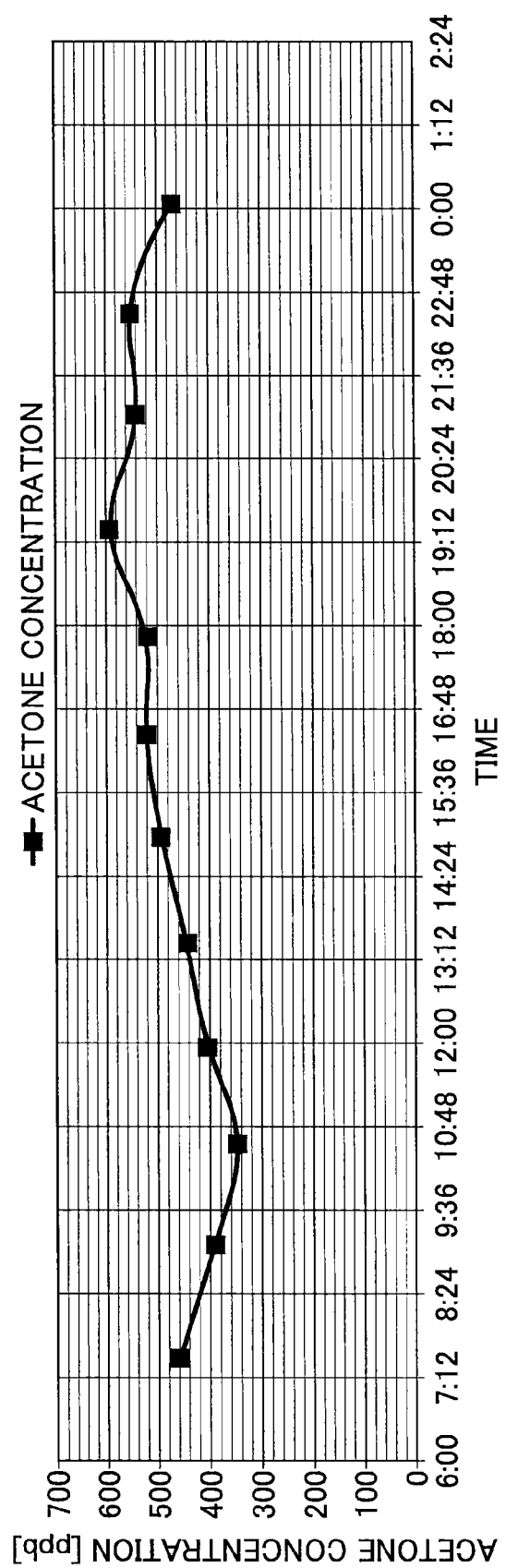
FIG. 8 shows an example of a graph which is calculated during the operations of the example 2 of the dieting support system according to the embodiment of the present invention.

The concentration of acetone in the biogas is measured by using the biogas sensor 200. The data of the measured concentration of acetone and the measurement time are transmitted from the communication unit 203 to the server 102. A graph such as shown in FIG. 8 is derived from the biogas concentration database 302 in the server 102. The graph is obtained by averaging fluctuation in the day of the concentration of acetone of the user in a predetermined time period. The measured concentration of acetone is compared with it. When the measured concentration of acetone is greater by a certain amount, a determination is made that it is a suitable state for the user to take the meal. The certain amount is calculated from the gender, the body fat percentage, the BMI, and a disease state of the personal information database 301. That is because an individual difference is generated in the certain amount by the gender, the body fat percentage, the BMI, and the disease state.

(I) A Case where a Determination is Made that it is the Suitable State to Take the Meal A message is transmitted to the user, which recommends taking the meal.

(II) A Case where a Determination is Made that it is not the Suitable State to Take the Meal A message is transmitted to the user, which implies that taking of the meal is to be refrained from for a while.

In the embodiment, similar to the embodiment 2, the message regarding the recommended meal and exercise, and the message to prevent excessive dieting may be transmitted.

Embodiment 4

An Example 3 of Operations of the Dieting Support System

A graph of fluctuation in the day such as shown in FIG. 9 is derived from the biogas concentration database 302. The graph is obtained by averaging fluctuation in the day of the concentration of acetone of the user in a predetermined time period. From this graph, it is found that, at what time of the day, the concentration of acetone of the user tends to become high. By notifying the user of the found time by the message, the suitable time of the day for the user for doing the exercise can be understood, without measuring the concentration of the acetone each time.

Embodiment 5

An Example 4 of Operations of the Dieting Support System

By reporting, by the fat-burning condition/exercise quantity estimation unit 305, information that quantifies and that classifies, in terms of fat-burning levels (the specific method is described in the embodiment 7—quantification methods of a fat burning condition and a quantity of exercise), the fat-burning condition of the user during one day or in a specific time period to the user through the display unit 202 at any time or at predetermined time which is decided by the user, during receiving the message by the terminal devices 100a and 100b, or during the measurement by the user of the concentration of the biogas, it can be understood what was the fat-burning condition in the past. By doing this, the user can easily understand whether the user's own daily acetone concentration level is improved or not, thereby facilitating to improve the contents of the executed exercise and the lifestyle.

Embodiment 6

An Example 5 of Operations of the Dieting Support System

During the measurement of the concentration of acetone in the biogas by the biogas sensor 200, variation of the concentration of acetone on the day of the measurement or variation of the concentration of acetone from the time at which the concentration of acetone is measured to specific time is estimated from the data of the concentration of acetone in the past, which is recorded in the biogas concentration database 302, thereby estimating the fat-burning condition on the day of the measurement or until the specific time. That is because, for a case where a living/behaving condition is constant, in the variation of the concentration of acetone in the biogas, a tendency is observed which is specific to the individual. Accordingly, it is possible to predict it to a certain extent. As a concrete prediction method, a graph is produced, which reflects the variation of the waveform in the past and which estimates the variation of the concentration of acetone, from the variation of the waveform of the graph of fluctuation in the day in which the variation of the concentration of acetone in the predetermined time period defined by the user is averaged, such as shown in FIG. 9, and from the measured concentration of acetone. With this, the user can understand the fat-burning condition on the date of the measurement or from the time of the measurement to the specific time by measuring the concentration of acetone only once, provided that a certain amount of data of the acetone concentration is accumulated in the past. In this manner, it can be easily determined whether the user's current lifestyle or the contents of the exercise are suitable in regard to the goal of the dieting, which is to be accomplished by the user.

Embodiment 7

Quantification Methods of a Fat Burning Condition and a Quantity of Exercise From the graph of fluctuation in the day, in which the variation of the concentration of acetone in the predetermined time period defined by the user is averaged, the fat-burning condition can be quantified as follows.

In Patent Document 1, the-fat burning condition at specific time is quantified and classified only from the concentration of acetone at the specific time, and Patent Document 1 does not disclose a method of quantifying and classifying the fat-burning condition in a specific time period. For example, for a case of quantifying the fat-burning condition from 7:00 a.m. to 12:00 a.m., quantification is possible by calculating an area of the graph of the concentration of acetone from 7:00 a.m. to 12:00 a.m. This value of the area is not directly indicating a decreased quantity of the fat. However, it indicates that, the greater this value is, the greater the level of the daily acetone concentration level becomes. Accordingly, it may be interpreted that, the greater this value is, the easier the fat is burned in the body. Further, by classifying the fat-burning level of the fat-burning condition of the user by the value of the area, it can be easily determined what the fat-burning condition of the user was. As a classification method, for example, the following is considered such that, when the value of the area is less than or equal to A, a level is one, that is, a condition where the fat is difficult to be burned or the fat is not burned; when the value of the area is greater than or equal to A and less than B, the level is two, that is, the condition where the fat is slightly burnable or the fat is slightly burned; and when the value of the area is greater than or equal to B, the level is three, that is, the condition where the fat is easily burnable or the fat is burned ($B \geq A$). Further, from the value of the area, or by combining the value of the area with the body fat percentage, the heart rate, and the oxygen intake which are calculated, for example, by the bioimpedance measurement, an amount of fat burning and the quantity of the exercise can be quantified.

Modified Example 1

In the embodiment 2, when results are frequently observed in a predetermined time period such that the measured concentration of acetone is significantly high, if the measured concentration of acetone is compared with the predetermined threshold value of the concentration of acetone, though the meal is taken within the predetermined time period, it is possible that the dieting is done excessively, or there is a possibility of having diabetes. Thus, a message may be transmitted to the user which prompts to terminate the excessive dieting or which prompts to receive medical treatment at a hospital. This modified example 1 can also be used for determining malnutrition. It may contribute to preventing the malnutrition of an aged person, where it is supposed that one in six people is a malnourished person.

Modified Example 2

The information regarding the recommended meal in the embodiment 2 may be reported to the user not only during reporting of the message which recommends taking the meal to the user, but also prior to the usual time at which the user takes the daily meal, or at any time desired by the user.

Modified Example 3

The recommended exercise of the embodiment 2 may be the exercise where aerobic exercise and anaerobic exercise are combined. It is known that the exercise where the aerobic exercise and the anaerobic exercise are combined is effective for burning the fat.

Modified Example 4

When the measured concentration of acetone is less than the predetermined threshold value of the concentration of acetone, since the state is such that the decomposition of the body fat is not promoted, the message that prompts to take the meal is not reported to the user. However, when the user desires to take the meal and to know the information regarding the recommended meal, a message may be transmitted which recommends the meal, which is low calorie food and in which the distribution ratio of carbohydrates is lower than the generally recommended distribution ratio.

Modified Example 5

Nitric monoxide discharged from any of the breath, the skin, and the mucous membrane functions as an expansion factor to smooth muscles of a bronchial tube, an intestinal tract, and a blood vessel. It is known that it is closely related to the metabolism. The measurement of the concentration of acetone may be performed concurrently with the measurement of the concentration of nitric monoxide, and the fat-burning condition may be comprehensively determined based on these measurement results.

Modified Example 6

The fat-burning condition may be determined by a ratio between oxygen and carbon dioxide which are discharged from any of the breath, the skin, and the mucous membrane.

Hereinabove, the dieting support system, the terminal device, the server, and the dieting support method are explained by the embodiments. However, the present invention is not limited to the above-described embodiments, and various modifications and improvements may be made within the scope of the present invention. Specific examples of numerical values are used in order to facilitate understanding of the invention. However, these numerical values are simply illustrative, and any other appropriate values may be used, except as indicated otherwise. The separations of the embodiments or the items are not essential to the present invention. Depending on necessity, subject matter described in two or more items may be combined and used, and subject matter described in an item may be applied to subject matter described in another item (provided that they do not contradict). For the convenience of explanation, the devices according to the embodiments of the present invention are explained by using functional block diagrams. However, these devices may be implemented in hardware, software, or combinations thereof. The software may be prepared in any appropriate storage medium, such as a random access memory (RAM), a flash memory, a read-only memory (ROM), an EPROM, an EEPROM, a register, a hard disk drive (HDD), a removable disk, a CD-ROM, a database, a server, and the like.

The present application claims priority based on Japanese Patent Application No. 2011-201180, filed on Sep. 14, 2011, the entire contents of which are hereby incorporated by reference.

LIST OF REFERENCE SYMBOLS 100a, 100b: Terminal devices
101: Network
102: Server
200: Biogas sensor
201: Operations unit
202: Display unit
203: Communication unit
300: Database
301: Personal information database
302: Biogas concentration database
303: Communication unit
304: Notification determination unit
305: Fat-burning condition/exercise quantity estimation unit
1000: Dieting support system
1001: Measurement function
1002: Analyzing function
1003: Timing determination function
1004: Notification function
1005: Meal-intake determination function
1006: Effect determination function
1007: Exercise execution determination function
1008: Calculation function
2000: Terminal device
2001: Measurement function
2002: Analyzing function
2003: Meal timing determination function
2004: Meal determination function
2005: Exercise timing determination function
2006: Exercise determination function
2007: Calculation function
2008: Notification function
2009: Transmitting function
2010: Receiving function
2011: Display function
3000: Server
3001: Receiving function
3002: Analyzing function
3003: Determination function
3004: Transmitting function

The invention claimed is:

1. A dieting support system comprising:
a terminal device comprising
a selective semiconductor gas sensor configured to detect a component of biogas and that measures concentration of the biogas; and
a communication interface configured to transmit a measured result by the selective semiconductor gas sensor to a server; and
the server comprising
an analyzing function that accumulates and analyzes a measured result by the selective semiconductor gas sensor;
a timing determination function that determines timing for taking a meal or for doing exercise, depending on an analyzed result by the analyzing function; and
a meal-intake determination function that determines whether the meal is taken within a predetermined time period, wherein when the timing determination function determines, based on the analyzed result by the analyzing function, that it is the timing for taking the meal or for doing the exercise, and when the meal-intake determination function determines that the meal is not taken within the predetermined timer period, a message which recommends taking the meal is sent from the server to the terminal device, and when the timing determination function determines, based on the analyzed result by the analyzing function, that it is the timing for taking the meal or for doing the exercise, and when the meal-intake determination function determines that the meal is taken within the predetermined time period, a message which recommends dong the exercise is sent from the server to the terminal device.

2. The dieting support system according to claim 1, wherein the biogas is acetone, wherein the analyzing function compares a measured result of concentration of the acetone with a predetermined threshold value, or compares the measured result of the concentration of the acetone with a result of accumulating the concentration of the acetone which is measured in a past, wherein the timing determination function determines the timing for taking the meal or for doing the exercise, depending on the analyzed result by the analyzing function, and wherein the server further includes a notification function that sends a message regarding the timing for taking the meal or for doing the exercise, a recommended meal, a recommended exercise, or a recommended lifestyle to the terminal device.

3. The dieting support system according to claim 1, wherein the meal-intake determination function performs detection of a rise of concentration of one or more gas components among ethanol, methyl mercaptan, and hydrogen sulfide; reference to electronic schedule data; reference to a blog or manually input data; or a combination thereof.

4. The dieting support system according to claim 1, wherein the server further comprises:

an effect determination function that determines whether there is an effect of the exercise, wherein the exercise is done in a past, wherein, when the effect determination function determines that there is the effect of the exercise, a message is sent from the server to the terminal device, wherein the message recommends doing the exercise at exercise intensity and for an exercise time period which are a same as those of a previous time, and wherein, when the effect determination function determines that there is no effect of the exercise, a message is sent from the server to the terminal device, wherein the message recommends doing the exercise while increasing the exercise intensity or extending the exercise time period.

5. The dieting support system according to claim 4, wherein the determination by the effect determination function is based on whether a total amount or an average value of the acetone in a predetermined time period after the exercise which is done in the past is increased compared to the total amount or the average value of the acetone in the predetermined time period prior to the exercise which is done in the past.

6. The dieting support system according to claim 1, wherein the server further comprises:

an exercise execution determination function that determines whether the exercise is done within a predetermined time period, wherein, when the exercise execution determination function determines that the exercise is not done, a message is sent from the server to the terminal device, wherein the message recommends doing the exercise.

7. The dieting support system according to claim 6, wherein the exercise execution determination function is based on any of detection of an increase in the concentration of the acetone or concentration of isoprene, wherein the acetone or the isoprene is discharged from a living body; reference to pedometer data;

reference to active mass meter data; reference to electronic schedule data; and reference to a blog or manually input data; or a combination thereof.

8. The dieting support system according to claim 1, wherein the server further comprises:

a calculation function that calculates, from a total amount of the acetone, a fat-burning condition in a predetermined time period, wherein a calculated result by the calculation function is sent from the server to the client terminal.

9. The dieting support system according to claim 1, wherein the component of the biogas is discharged from one or more of breath, skin, or a mucous membrane, wherein the component of the biogas is at least one of selected from a group including the acetone, ethanol, methyl mercaptan, hydrogen sulfide, isoprene, nitric monoxide, oxygen, and carbon dioxide, and wherein the measurement function that detects the component of the biogas and that measures the concentration of the biogas detects the component of the biogas and measures the concentration of the biogas at a predetermined time interval or at any timing by using one or more types of sensors.

10. A terminal device comprising:

a selective semiconductor gas sensor configured to detect biogas and that measures concentration of the biogas;

a transmitting function that transmits the measured result to outside;

a receiving function that receives a message regarding timing for taking a meal or doing exercise, a recommended meal, a recommended exercise, a recommended lifestyle, or a fat-burning condition;

a display function that displays the received message;

an analyzing function that accumulates and analyzes a measured result of the detected biogas;

a timing determination function that determines the timing for taking the meal;

a meal determination function that determines information regarding the recommended meal;

an exercise execution timing determination function that determines the timing for doing the exercise;

an exercise determination function that determines exercise intensity and an exercise time period;

a calculation function that determines the fat-burning condition; and a notification function that sends the message regarding the timing for taking the meal or ding the exercise, the message regarding the information on the recommended meal, a message regarding the exercise intensity, a message regarding the exercise time period, or the message regarding the fat-burning condition.

11. A server comprising:
- a receiving function that receives a measured result of biogas by a selective semiconductor gas sensor, wherein the biogas is discharged from a living body;
- an analyzing function that accumulates and analyzes the received measured result of the biogas;
- a determination function that determines timing for taking a meal or for doing exercise, a recommended meal, a recommended exercise, a recommended lifestyle, or a fat-burning condition, wherein the determination function further determines whether the meal is taken within a predetermined time period; and
  - a transmitting function that transmits a message regarding the timing for taking the meal or doing the exercise, the recommended meal, the recommended exercise, the recommended lifestyle, or the fat-burning condition,
- wherein, when the determination function determines, based on the analyzed result by the analyzing function, that it is the timing for taking the meal or for doing the exercise, and when the determination function determines that the meal is not taken within the predetermined time period, the transmitting function transmits a message which recommends taking the meal, and
- wherein, when the determination function determines, based on the analyzed result by the analyzing function, that it is the timing for taking the meal or for doing the exercise, and when the determination function determines that the meal is taken within the predetermined time period, the transmitting function transmits a message which recommends doing the exercise.

12. A dieting support method that causes a computer to execute:
- a measurement step performed by a selective semiconductor gas sensor of detecting a component of biogas and measuring concentration of the component of the biogas, wherein the component of the biogas is discharged from a living body;
- an analyzing step of accumulating and analyzing a measured result by the measurement step;
- a timing determination step of determining timing for taking a meal or doing exercise, a recommended meal, depending on an analyzed result of the analyzing step; and
- a meal-intake determination step of determining whether the meal is taken within a predetermined time period,
- wherein, when the timing determination step determines, based on the analyzed result by the analyzing step, that it is the timing for taking the meal or for doing the exercise, and when the meal-intake determination step determines that the meal in not taken within the predetermined time period, a message which recommends taking the meal is send, and
- wherein, when the timing determination step determines, based on the analyzed result by the analyzing step, that it is the timing for taking the meal or for doing the exercise, and when the meal-intake determination step determines that the meal is taken within the predetermined time period, a message which recommends doing the exercise is sent.

* * * * *